United States Patent
Stark

[19]

[11] Patent Number: 6,044,504

[45] Date of Patent: Apr. 4, 2000

[54] PATIENT SUPPORT FOR A SCINTILLATION CAMERA

[75] Inventor: Iain Stark, Nepean, Canada

[73] Assignee: IS2 Research, Inc., Ontario, Canada

[21] Appl. No.: 09/127,985

[22] Filed: Aug. 3, 1998

[30] Foreign Application Priority Data

Aug. 1, 1997 [CA] Canada .................................. 2212196

[51] Int. Cl.[7] ...................................................... A61B 6/04
[52] U.S. Cl. .................................. 5/601; 5/943; 378/208
[58] Field of Search ............................. 5/601, 943, 626; 378/209, 208; 250/363.08

[56] References Cited

U.S. PATENT DOCUMENTS

| | | | |
|---|---|---|---|
| 3,050,745 | 8/1962 | Tabbert ........................................ | 5/86.1 |
| 3,765,549 | 10/1973 | Jones . | |
| 4,064,441 | 12/1977 | Casale . | |
| 4,131,802 | 12/1978 | Braden et al. ........................ | 378/208 X |
| 4,216,381 | 8/1980 | Lange . | |
| 4,223,222 | 9/1980 | Gray et al. . | |
| 4,651,007 | 3/1987 | Perusek et al. . | |
| 4,774,411 | 9/1988 | Span ..................................... | 250/363.08 |
| 5,047,641 | 9/1991 | Besseling et al. . | |
| 5,146,094 | 9/1992 | Stark . | |
| 5,262,648 | 11/1993 | Stark . | |
| 5,808,468 | 9/1998 | Bis et al. ................................. | 5/601 X |
| 5,866,906 | 2/1999 | Jensen ............................. | 250/363.08 X |
| 5,960,054 | 9/1999 | Freeman et al. ............................. | 378/4 |

FOREIGN PATENT DOCUMENTS

| | | | |
|---|---|---|---|
| 209326 | 1/1987 | European Pat. Off. .................... | 5/601 |

Primary Examiner—Terry Lee Melius
Assistant Examiner—Rodrigo J. Morales
Attorney, Agent, or Firm—Finnegan, Henderson, Farabow, Garrett & Dunner, L.L.P.

[57] ABSTRACT

A patient support is designed for use with a scintillation camera that includes a vertically oriented annular rotating support having an axis, and an elongate support extending from the rotating support for supporting a detector head, the rotating support including a coaxial inner surface defining an orifice. The patient support includes a patient stretcher for supporting a patient in a horizontal position substantially parallel to the axis of the rotating support. The patient support also includes a detached support for horizontally supporting the patient stretcher on a ground surface. The detached support includes a first stretcher support for supporting the patient stretcher and for positioning the patient stretcher relative to the rotating support. The patient support also includes an engaged support for horizontally supporting the patient stretcher on the inner surface of the cylindrical support such that the patient stretcher remains unaffected by the rotation of the rotating support. The engaged support includes a second stretcher support for supporting the patient stretcher and for positioning the patient stretcher relative to the rotating support.

10 Claims, 9 Drawing Sheets

PATIENT SUPPORT FOR A SCINTILLATION CAMERA

FIELD OF INVENTION

The present invention relates to a patient support for a scintillation camera. In particular, the invention relates to an apparatus for supporting a patient and for positioning a patient relative to a scintillation camera including a gantry having a rotating annular support.

BACKGROUND OF THE INVENTION

In the human body, increased metabolic activity is associated with an increase in emitted radiation. In the field of nuclear medicine, increased metabolic activity within a patient is detected using a radiation detector such as a scintillation camera.

Scintillation cameras are well known in the art, and are used for medical diagnostics. A patient ingests, or inhales or is injected with a small quantity of a radioactive isotope. The radioactive isotope emits photons that are detected by a scintillation medium in the scintillation camera. The scintillation medium is commonly a sodium iodide crystal, BGO or other. The scintillation medium emits a small flash or scintillation of light, in response to stimulating radiation, such as from a patient. The intensity of the scintillation of light is proportional to the energy of the stimulating photon, such as a gamma photon. Note that the relationship between the intensity of the scintillation of light and the gamma photon is not linear.

A conventional scintillation camera such as a gamma camera includes a detector which converts into electrical signals gamma rays emitted from a patient after radioisotope has been administered to the patient. The detector includes a scintillator and photomultiplier tubes. The gamma rays are directed to the scintillator which absorbs the radiation and produces, in response, a very small flash of light. An array of photodetectors, which are placed in optical communication with the scintillation crystal, converts these flashes into electrical signals which are subsequently processed. The processing enables the camera to produce an image of the distribution of the radioisotope within the patient.

Gamma radiation is emitted in all directions and it is necessary to collimate the radiation before the radiation impinges on the crystal scintillator. This is accomplished by a collimator which is a sheet of absorbing material, usually lead, perforated by relatively narrow channels. The collimator is detachably secured to the detector head, allowing the collimator to be changed to enable the detector head to be used with the different energies of isotope to suit particular characteristics of the patient study. A collimator may vary considerably in weight to match the isotope or study type.

Scintillation cameras are used to take four basic types of pictures: spot views, whole body views, partial whole body views, SPECT views, and whole body SPECT views.

A spot view is an image of a part of a patient. The area of the spot view is less than or equal to the size of the field of view of the gamma camera. In order to be able to achieve a full range of spot views, a gamma camera must be positionable at any location relative to a patient.

One type of whole body view is a series of spot views fitted together such that the whole body of the patient may be viewed at one time. Another type of whole body view is a continuous scan of the whole body of the patient. A partial whole body view is simply a whole body view that covers only part of the body of the patient. In order to be able to achieve a whole body view, a gamma camera must be positionable at any location relative to a patient in an automated sequence of views.

The acronym "SPECT" stands for single photon emission computerized tomography. A SPECT view is a series of slice-like images of the patient. The slice-like images are often, but not necessarily, transversely oriented with respect to the patient. Each slice-like image is made up of multiple views taken at different angles around the patient, the data from the various views being combined to form the slice-like image. In order to be able to achieve a SPECT view, a scintillation camera must be rotatable around a patient, with the direction of the detector head of the scintillation camera pointing in a series of known and precise directions such that reprojection of the data can be accurately undertaken.

A whole body SPECT view is a series of parallel slice-like transverse images of a patient. Typically, a whole body SPECT view consists of sixty four spaced apart SPECT views. A whole body SPECT view results from the simultaneous generation of whole body and SPECT image data. In order to be able to achieve a whole body SPECT view, a scintillation camera must be rotatable around a patient, with the direction of the detector head of the scintillation camera pointing in a series of known and precise directions such that reprojection of the data can be accurately undertaken.

Therefore, in order that the radiation detector be capable of achieving the above four basic views, the support structure for the radiation detector must be capable of positioning the radiation detector in any position relative to the patient. Furthermore, the support structure must be capable of moving the radiation detector relative to the patient in a controlled manner along any path.

In order to operate a scintillation camera as described above, the patient should be supported horizontally on a patient support or stretcher.

The detector head of the scintillation camera must be able to pass underneath the patient. Therefore, in order for the scintillation camera to generate images from underneath the patient, the patient support must be thin. However, detector heads are generally supported by a pair of arms which extend from a gantry. Thus, the patient support generally must be cantilevered in order for the detector head to be able to pass underneath the patient without contacting any supporting structure associated with the patient support. The design of a cantilevered patient support that is thin enough to work properly with a scintillation camera is exceedingly difficult. Expensive materials and materials that are difficult to work with, such as carbon fiber, are often used in the design of such cantilevered patient supports.

A certain design of gantry or support structure for a scintillation camera includes a frame upon which a vertically oriented annular support rotates. Extending out from the rotating support is an elongate support. The elongate support generally comprises a pair of arms. The pair of arms generally extends through a corresponding pair of apertures in the rotating support. One end of the pair of arms supports the detector head on one side of the annular support. The other end of the pair of arms supports a counter balance weight. Thus, the elongate support is counterbalanced with a counterweight on the opposite side of the detector head.

With such a design of support structure for a scintillation camera, a patient must lie on a horizontally oriented patient support. The patient support must be cantilevered so that the detector head can pass underneath the patient. If the detector head must pass underneath only one end of the patient, such as the patient's head, the cantilevered portion of the patient support is not long enough to cause serious difficulties in the design of the cantilevered patient support. However, if the camera must be able to pass under the entire length of the patient, the entire patient must be supported by the cantilevered portion of the patient support. As the cantilevered portion of the patient support must be thin so as not to interfere with the generation of images by the scintillation camera, serious design difficulties are encountered.

Among the advantages associated with such design of support structure is that a patient may be partially passed through the orifice defined by the annular support so that the pair of arms need not be as long. However, the patient support must be able to support the patient in this position relative to the annular support, must be accurately positionable relative to the annular support, and must not interfere either with the rotation of the annular support or with the cables which will inevitably extend from the detector head to a nearby computer or other user control.

SUMMARY OF THE INVENTION

An object of the present invention is to provide an improved patient support for a scintillation camera.

A second object of the present invention is to provide an improved patient support for use with a scintillation camera including a rotatable annular support for supporting and positioning a detector head.

The patient support of the present invention is designed for use with a scintillation camera that includes a vertically oriented annular rotating support having an axis, and an elongate support extending from the rotating support for supporting a detector head, the rotating support including a coaxial inner surface defining an orifice.

A patient support embodying the present invention includes a patient stretcher for supporting a patient in a horizontal position substantially parallel to the axis of the rotating support.

The patient support embodying the present invention also includes a detached support for horizontally supporting the patient stretcher on a ground surface. The detached support includes a first stretcher support for supporting the patient stretcher and for positioning the patient stretcher relative to the rotating support.

The patient support embodying the present invention also includes an engaged support for horizontally supporting the patient stretcher on the inner surface of the cylindrical support such that the patient stretcher remains unaffected by the rotation of the rotating support. The engaged support includes a second stretcher support for supporting the patient stretcher and for positioning the patient stretcher relative to the rotating support.

In an embodiment of the patient support of the present invention, the patient support includes a cylindrical support rigidly mountable to the inner surface of a rotating support. The cylindrical support is coaxial with and extends beyond the rotating support. The cylindrical support includes an inner surface, an outer surface, a circular front edge, and a circular rear edge.

The embodiment also includes a patient stretcher for supporting a patient in a horizontal position substantially parallel to the axis of the rotating support. The patient stretcher includes a flat lower surface and two parallel sides.

The embodiment also includes a detached support for horizontally supporting the patient stretcher on a ground surface. The detached support includes a first rigid frame. The detached support also includes floor rolling means for engaging a ground surface such that the first rigid frame is moveable relative to the ground surface. The floor rolling means includes a plurality of casters. The detached support also includes a brake for immobilizing the frame relative to the ground surface. The brake includes a plurality of extendable and retractable feet for selectively engaging the ground surface. The detached support also includes a first stretcher support for supporting the patient stretcher and for positioning the patient stretcher relative to the rotating support. The first stretcher support includes a plurality of parallel wheels in rolling engagement with the lower surface of the patient support. The first stretcher support also includes a pair of rails slidably engaging the sides of the patient support for horizontally stabilizing the patient support.

The embodiment also includes an engaged support for horizontally supporting the patient stretcher on the inner surface of the cylindrical support such that the patient stretcher remains unaffected by the rotation of the rotating support. The engaged support includes a second rigid frame. The engaged support also includes a transverse rolling means for engaging the inner surface of the rotating support. The transverse rolling means includes a plurality of parallel wheels for orienting perpendicularly to the axis of the rotating support in rolling engagement with the inner surface of the cylindrical support. The engaged support also includes a second stretcher support for supporting the patient stretcher and for positioning the patient stretcher relative to the rotating support. The second stretcher support includes a plurality of parallel wheels for rolling engagement with the lower surface of the patient support. The engaged support also includes a stabilizer for stabilizing the engaged support relative to the cylindrical support. The stabilizer also includes at least one wheel in rolling engagement with the outer surface of the cylindrical support. The stabilizer also includes at least one wheel in rolling engagement with the front edge of the cylindrical support. The stabilizer also includes at least one wheel in rolling engagement with the rear edge of the cylindrical support.

One advantage of the present invention is that there is provided an improved patient support for a scintillation camera. A second advantage is that there is provided an improved patient support for use with a scintillation camera including a rotatable annular support for supporting and positioning a detector head. A third advantage is that the patient stretcher need not be cantilevered to an extent that causes design difficulties. A fourth advantage is that the patient support can be thin so as not to interfere unduly with the generation of images by a scintillation camera positioned below a patient. A fifth advantage of the present invention is that a patient may be partially pass through the orifice defined by the annular rotating support so that the pair of arms need not be as long. A sixth advantage of the present invention is that the patient support may be accurately positioned relative to the annular support. A seventh advantage of the present invention is that the patient support does not interfere either with the rotation of the annular support or with the cables which will inevitably extend from the detector head to a nearby computer or other user control.

Other advantages, objects and features of the present invention will be readily apparent to those skilled in the art from a review of the following detailed descriptions of preferred embodiments in conjunction with the accompanying drawings and claims.

BRIEF DESCRIPTION OF THE DRAWINGS

The embodiments of the invention will now be described with reference to the accompanying drawings, in which.

Similar references are used in different figures to denote similar components.

DETAILED DESCRIPTION OF THE INVENTION

Figure 1:
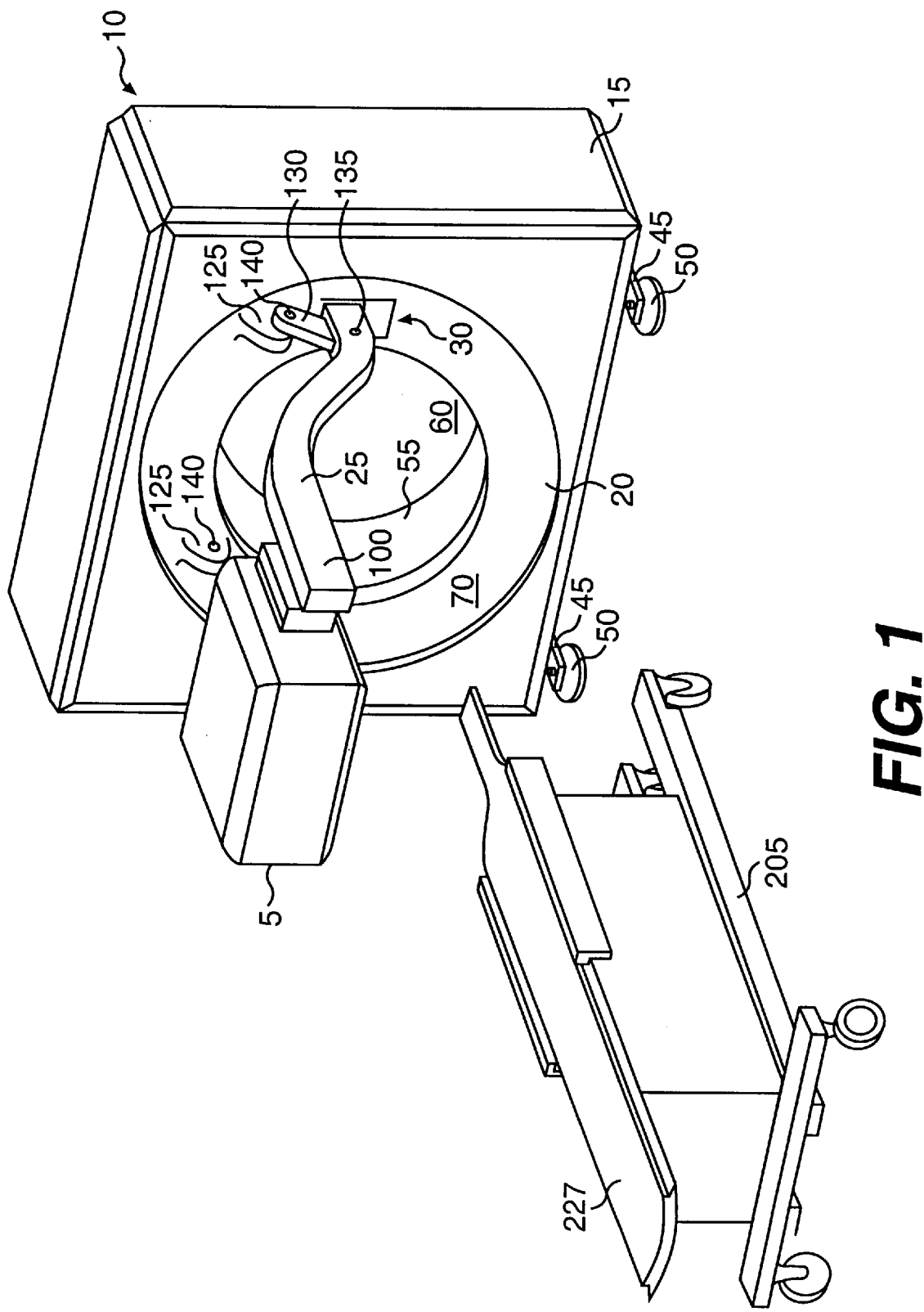
FIG. 1 is a perspective view of a scintillation camera including a detached patient support in accordance with the invention.
Figure 2:
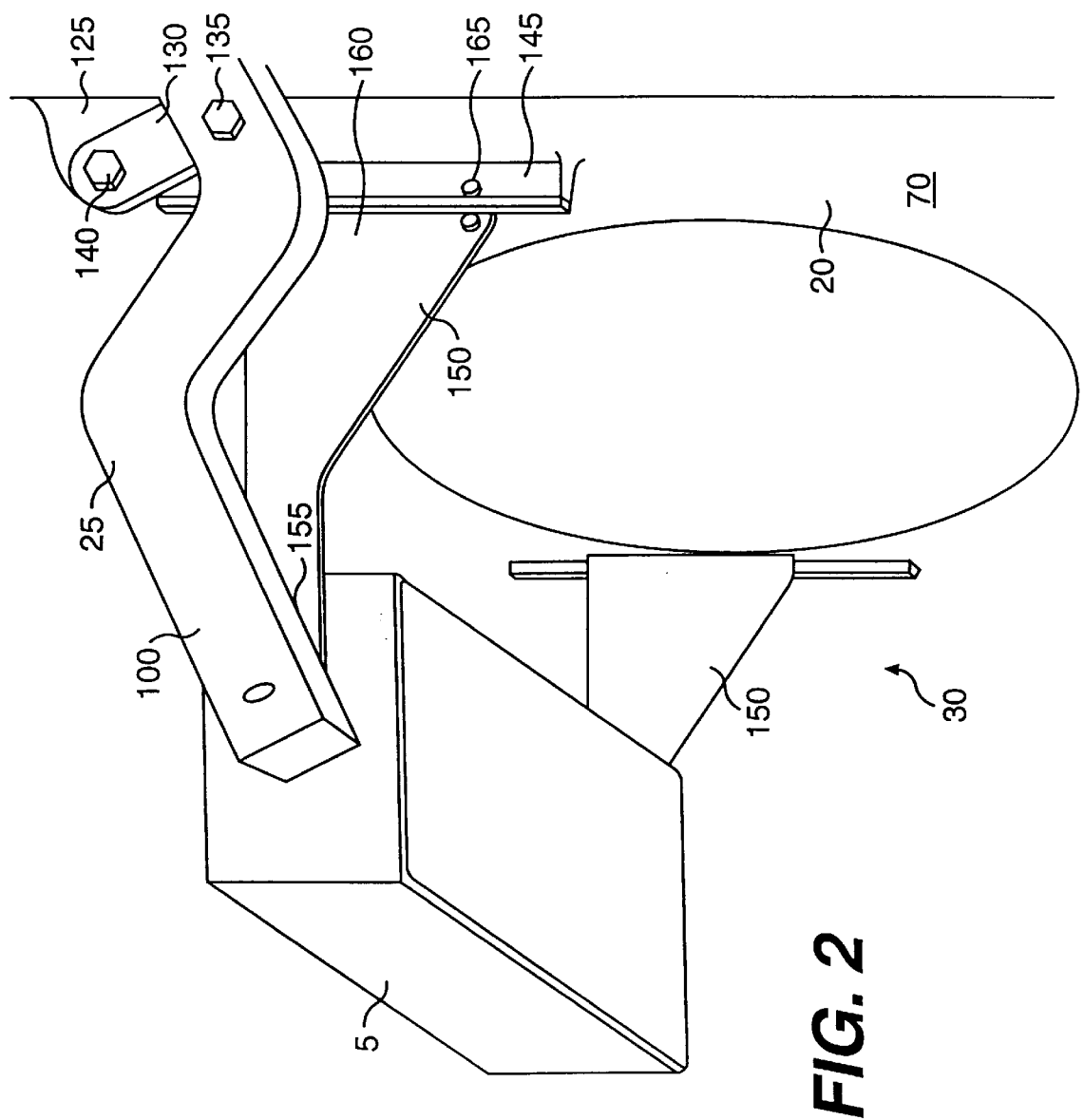
FIG. 2 is a perspective view of the guide of a scintillation camera.
Figure 3:
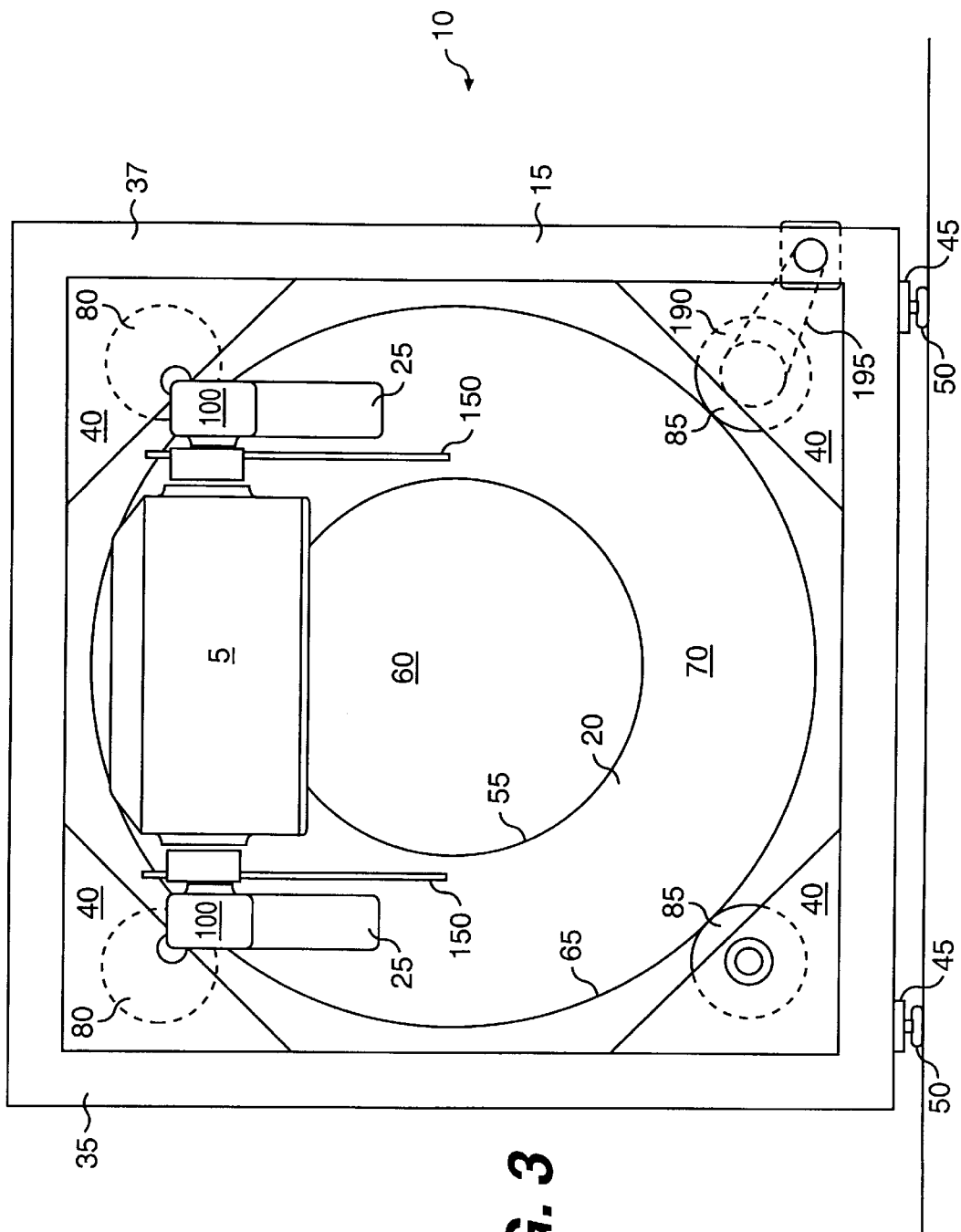
FIG. 3 is a front elevation view of a scintillation camera.
Figure 4:
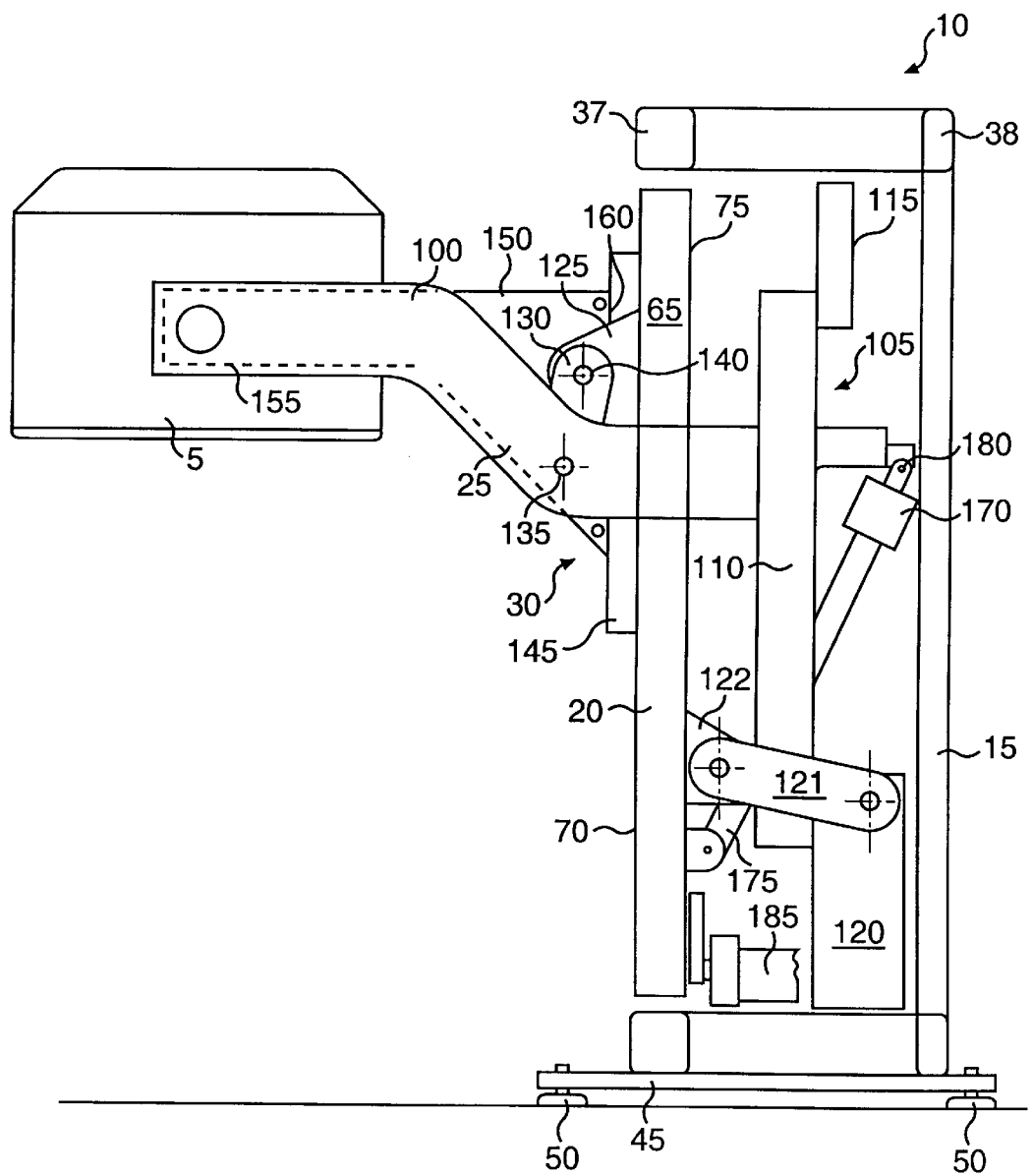
FIG. 4 is a side elevation view of a scintillation camera.
Figure 5:
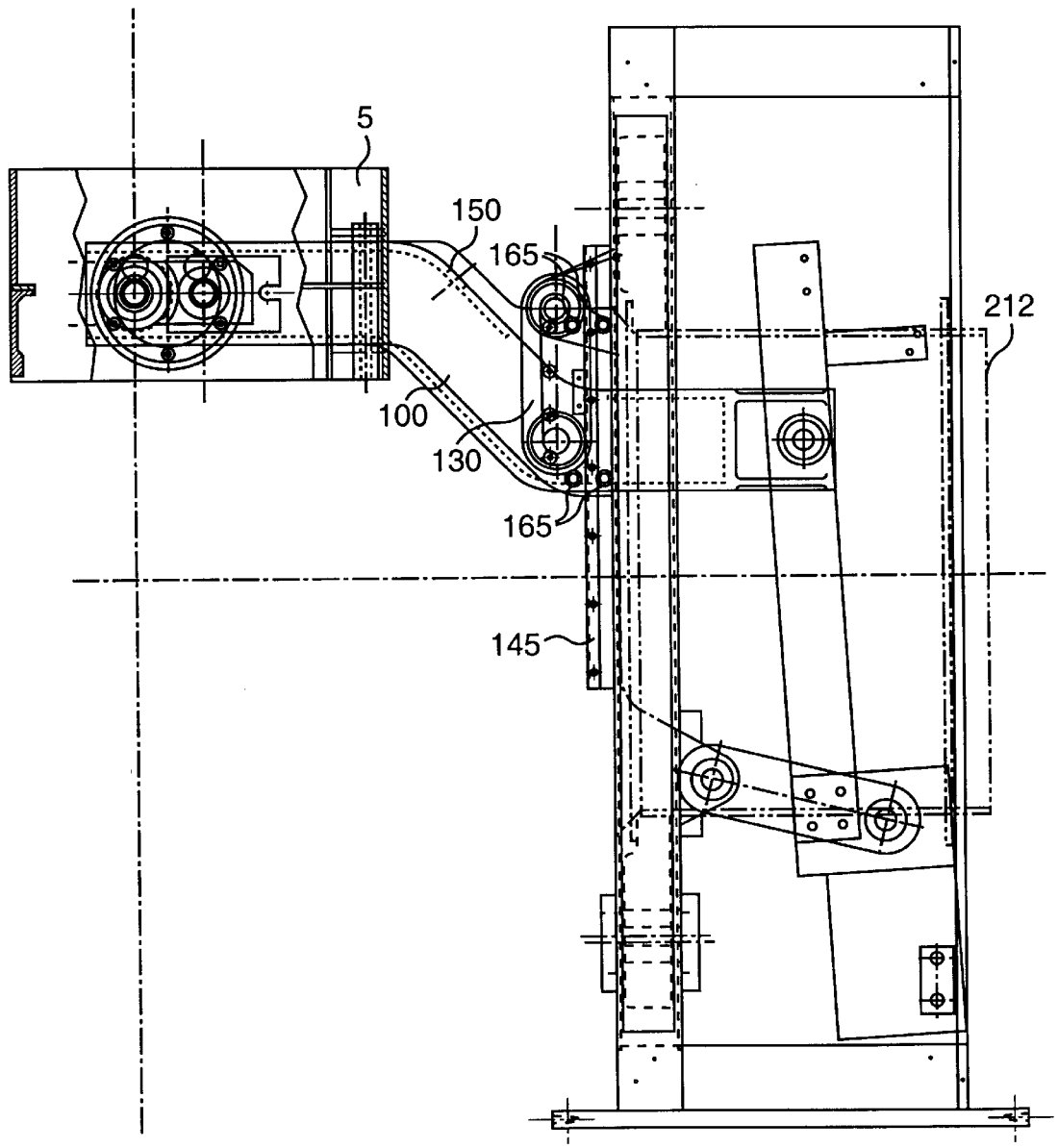
FIG. 5 is a side elevation view of a scintillation camera.
Figure 6:
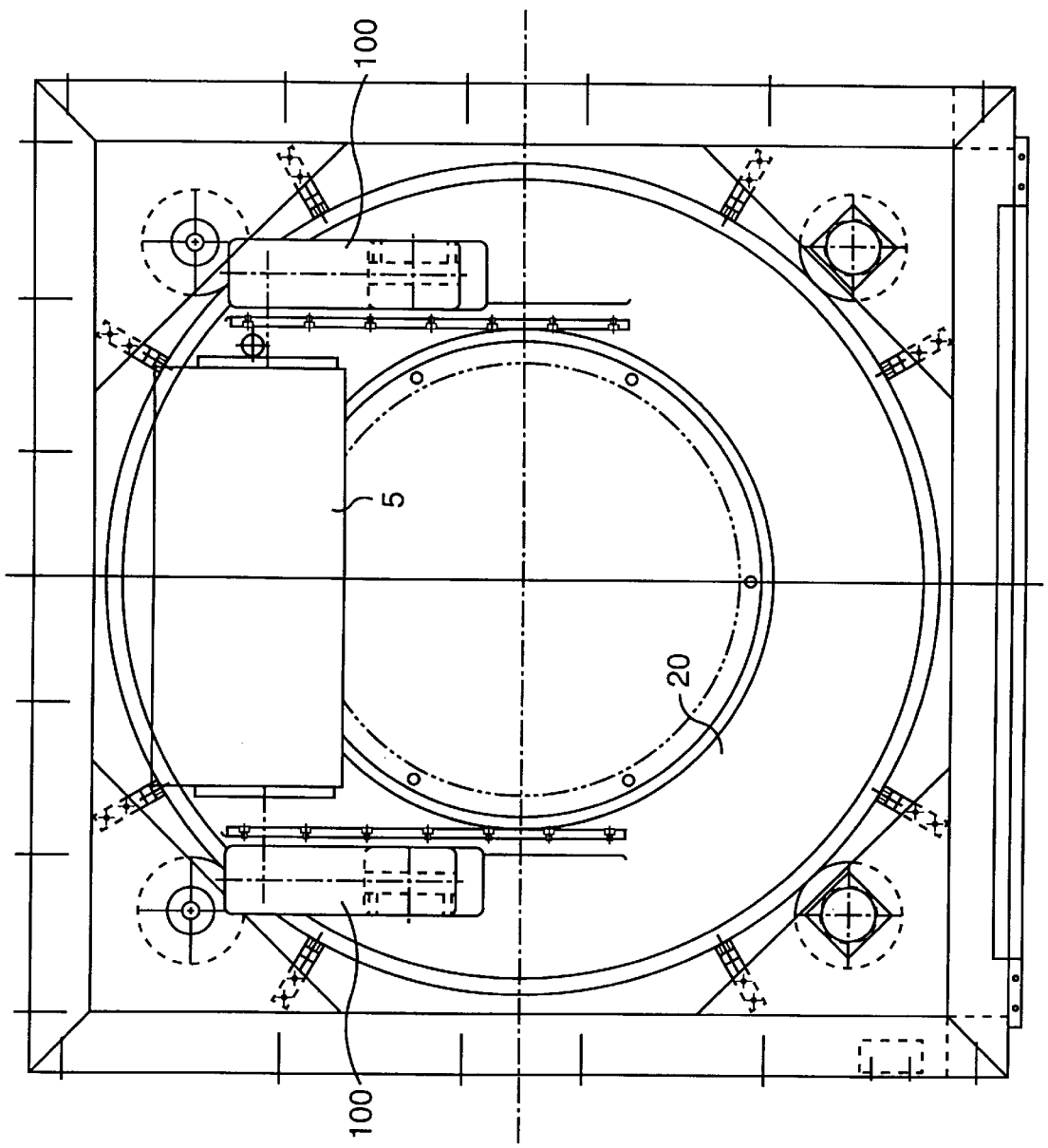
FIG. 6 is a front elevation view of a scintillation camera.
Figure 7:
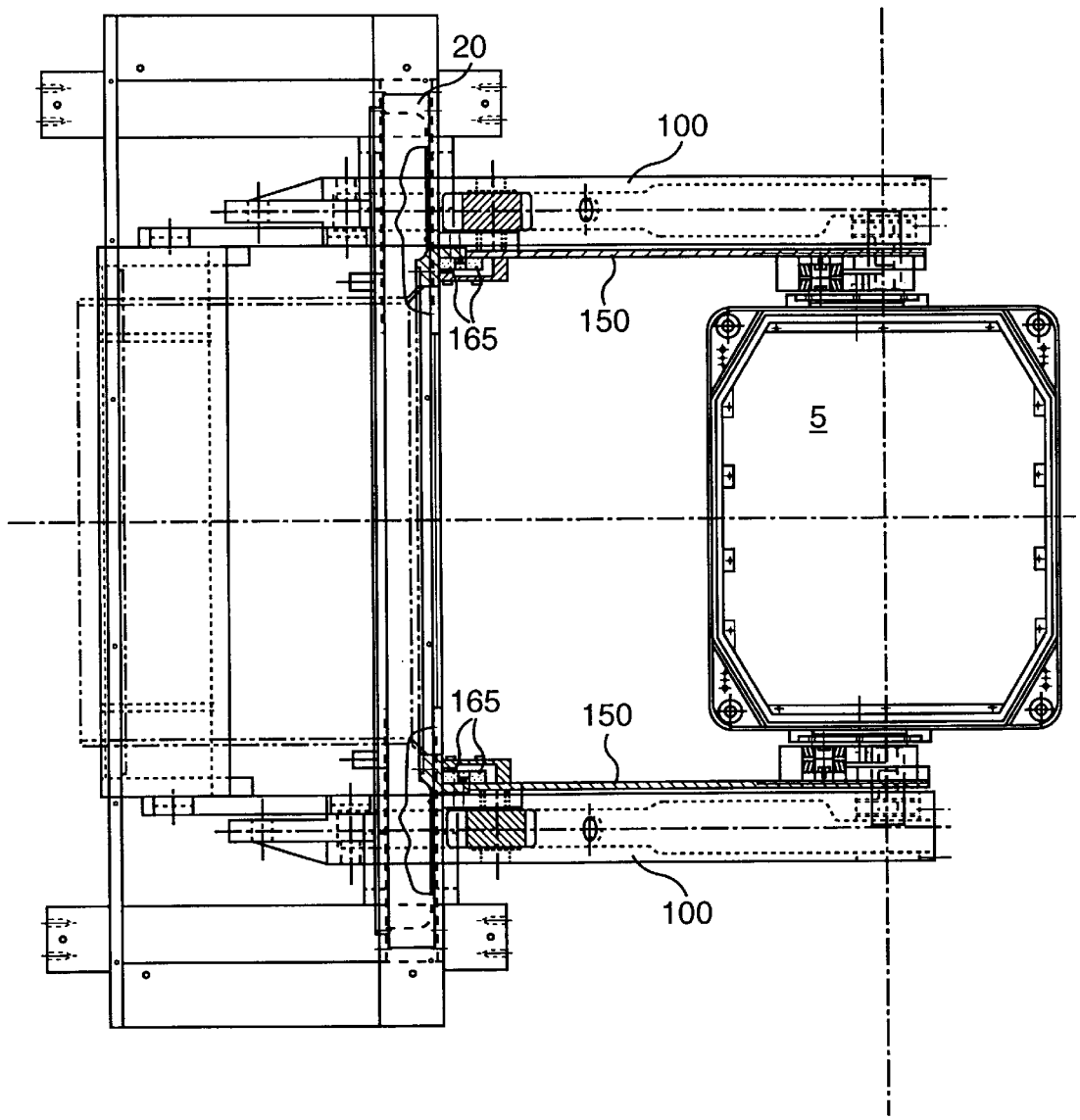
FIG. 7 is a top plan view of a scintillation camera.
Figure 8:
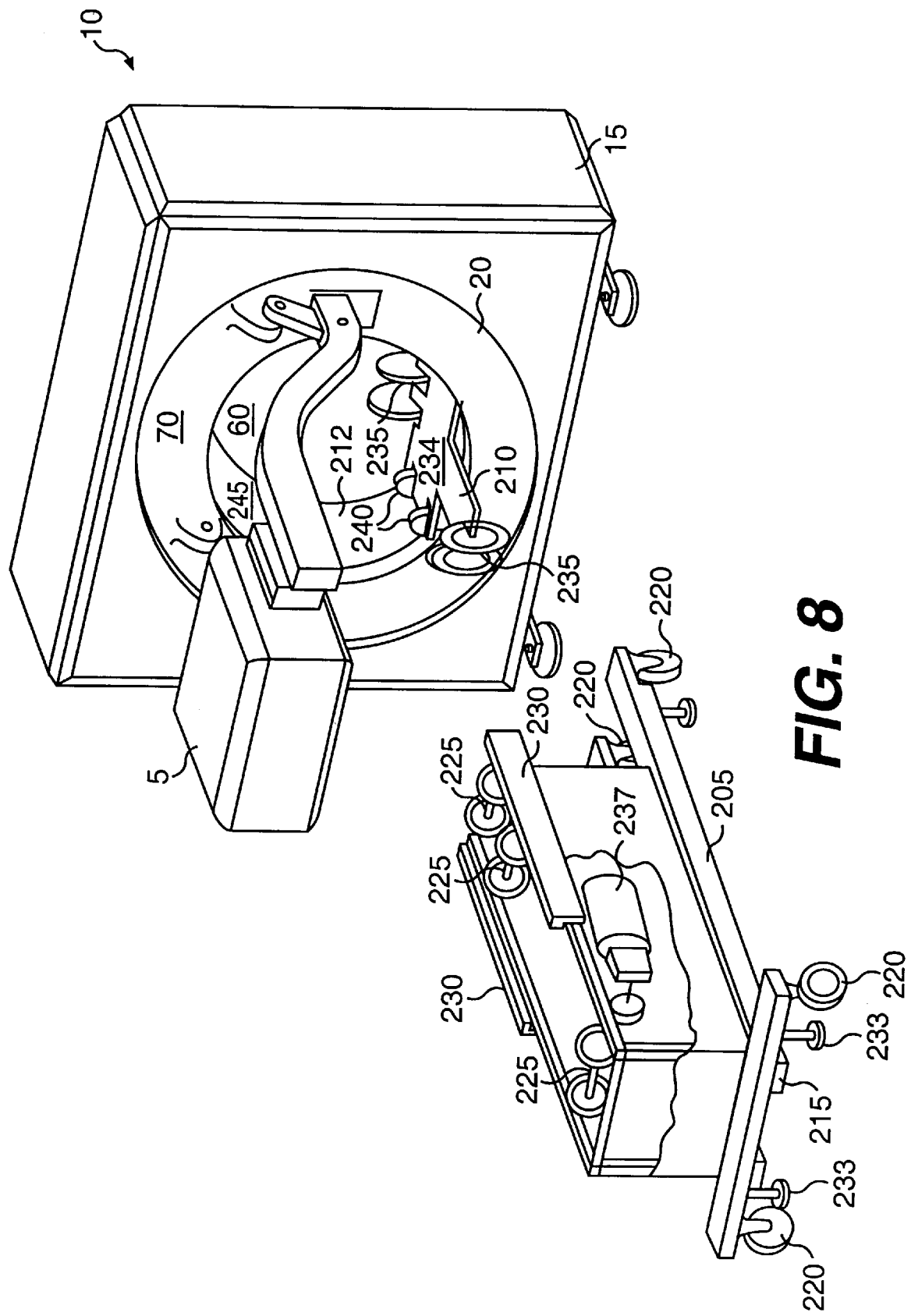
FIG. 8 is a perspective view of the scintillation camera of FIG. 1, including the detached patient support and engaged patient support, with the stretcher removed.
Figure 9:
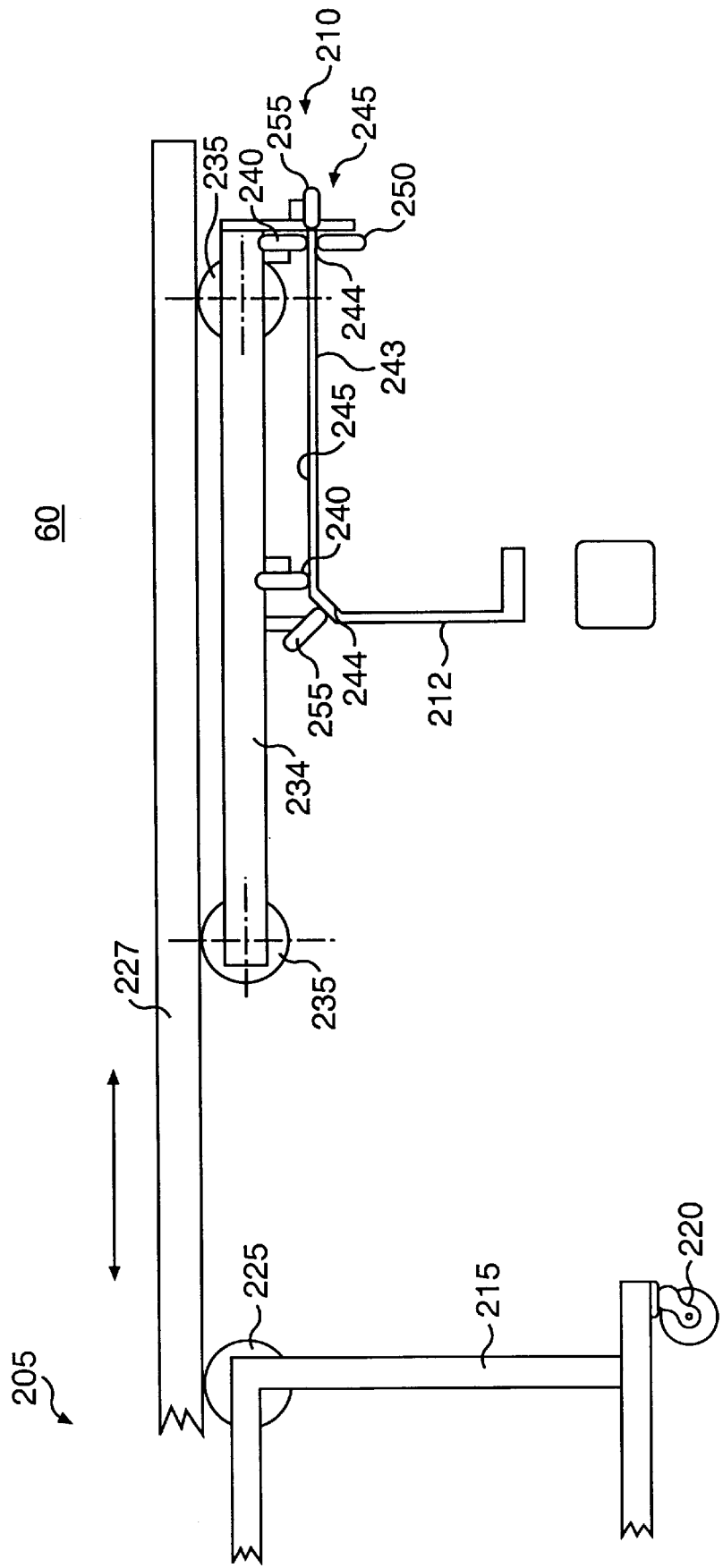
FIG. 9 is a side view of a portion of the patient support apparatus.

Referring to FIGS. 1 to 9, a nuclear camera 5 is supported and positioned relative to a patient by a support structure 10. Nuclear cameras are heavy, usually weighing approximately three to four thousand pounds. Thus, the support structure 10 should be strong and stable in order to be able to position the camera 5 safely and accurately. The support structure 10 includes a base 15, an annular support 20, an elongate support 25, and a guide 30.

The base 15 includes a frame 35. The frame 35 includes twelve lengths of square steel tubing welded together in the shape of a rectangular parallelepiped. The frame 35 has a front square section 37 and a rear square section 38. In the illustrated embodiment, the frame 35 is approximately five feet wide, five feet high, and two feet deep. The frame 35 also includes eight triangular corner braces 40 welded to the front square section 37, that is, each corner of the front square section 37 has two corner braces 40, one towards the front of the front square section 37, and one towards the rear of the front square section 37. In the illustrated embodiment, the corner braces 40 are in the shape of equilateral right angle triangles.

Attached to the underside of the frame 35 are two horizontal legs 45. Attached to each leg 45 are two feet 50. An alternative to the use of feet 50 is to attach the base 15 to a floor by way of bolts set into the floor. The legs 45 extend beyond the frame 35 so as to position the feet 50 wider apart to increase the stability of the base 15. The feet 50 are adjustable so that the base 15 may be levelled. Thus constructed, the base 15 is strong, stable, rigid, and capable of supporting heavy loads.

The annular support 20 is vertically oriented, having an inner surface 55 defining an orifice 60, an outer surface 65, a front surface 70, and a rear surface 75. The annular support 20 is constructed of a ductile iron casting capable of supporting heavy loads. In the illustrated embodiment, the annular support 20 has an outside diameter of about fifty two inches. The annular support 20 is supported by upper rollers 80 and lower rollers 85 which are mounted on the base 15. The upper rollers 80 and lower rollers 85 roll on the outer surface 65, thus enabling the annular support 20 to rotate relative to the base 15 in the plane defined by the annular support 20. Each of the upper rollers 80 and lower rollers 85 are mounted onto a pair of corner braces 40 by way of axles with deep groove bearings. The bearings should be low friction and be able to withstand heavy loads. The axles of the upper rollers 80 are radially adjustable relative to the annular support 20, so that the normal force exerted by the upper rollers 80 on the outer surface 60 is adjustable. The curved surfaces of the upper rollers 80 and lower rollers 85 (i.e. the surfaces that contact the outer surface 60) should be tough so as to be able to withstand the pressures exerted by the annular support 20, and should have a fairly high coefficient of friction so as to roll consistently relative to the annular support 20.

Attached to each pair of corner braces 40 is a stabilizing arm oriented perpendicularly to the plane of the annular support 20. A pair of small stabilizing rollers are mounted onto each stabilizing arm 90. Each pair of stabilizing rollers is positioned such that one stabilizing roller rolls on the front surface 70, and the other stabilizing roller rolls on the rear surface 75. The stabilizing rollers maintain the annular support 20 in the vertical plane.

The elongate support 25 includes a pair of support arms 100, each of which extends through an aperture in the annular support 20. The nuclear camera 5 is rotatably attached to one end of the pair of support arms 100, such that the nuclear camera 5 faces the front surface 70. A counter weight 105 is attached to the other end of the pair of support arms 100, such that the counterweight 105 faces the rear surface 75.

The counter weight 105 includes a pair of parallel counter weight members 110, each of which is pivotally attached to one of the support arms 100. A first weight 115 is attached to one end of the pair of counter weight members 110, and a second weight 120 is attached to the other end of the pair of counter weight members 110. A pair of counter weight links 121 connect the counter weight members 110 to the annular support 20. Each counter weight link 121 is pivotally attached at one end to its corresponding counter weight member 110. Each counter weight link 121 is pivotally attached at its other end to a counter weight bracket 122 which is rigidly attached to the annular support 20. The counter weight links 121 are attached to the counterweight members 110 and counter weight brackets 122 using bolts and tapered roller bearings. Each counter weight link 121 is pivotable relative to the annular support 20 in a plane perpendicular to and fixed relative to the annular support 20.

The guide 30 attaches the elongate support 25 to the annular support 20, and controls the position of the elongate support 25, and hence the scintillation camera 5, relative to the annular support 20. A pair of brackets 125 is rigidly attached to the annular support 20. A pair of rigid links 130 is pivotally attached at support arm pivot points 135 to the support arms 100. The pair of links 130 is also pivotally attached at bracket pivot points 140 to the brackets 125. At the support arm pivot points 135 and bracket pivot points 140 are tapered roller bearings mounted with bolts. Each link 130 is pivotable relative to the annular support 20 in a plane perpendicular to and fixed relative to the annular support 20. Thus, as the annular support 20 rotates relative to the base 15, the respective planes in which each link 130 and each support arm 100 can move remain fixed relative to the annular support 20.

A pair of linear tracks 145 are rigidly attached to the front surface 70 of the annular support 20. The tracks 145 are oriented such that they are parallel to the respective planes in which each link 130 and each support arm 100 can move. A pair of rigid sliding arms 150 (not shown in FIG. 1) include camera ends 155 and straight ends 160. Each camera end 155 is pivotally attached to one of the support arms 100 at the point of attachment of the scintillation camera 5. Each straight end 160 includes a pair of spaced apart cam followers or guides 165 slidable within the corresponding track 145. Thus, movement of the scintillation camera 5 relative to the annular support 20 (i.e. we are not concerned, at this point, with rotational movement of the scintillation camera 5 relative to the elongate support 25) is linear and parallel to the plane of the annular support 20. Note that if the camera ends 155 were pivotally attached to the support arms 100 between the nuclear camera 5 and the annular support 20, the movement of the nuclear camera 5 relative to the annular support 20 would not be linear.

Movement of the scintillation camera 5 relative to the annular support 20 is effected by an actuator 170. The actuator 170 includes a fixed end 175 pivotally attached to the annular support 20, and a movable end 180 pivotally attached to the elongate support 25. The actuator 170 is extendable and retractable, and is thus able to move the elongate support 25 relative to the annular support 20.

Movement of the annular support 20 relative to the base 15 is effected by a drive unit 185. The drive unit 185 includes a quarter horsepower permanent magnet DC motor and a gearbox to reduce the speed of the output shaft of the drive unit 185. Alternatively, other types of motors could be used, such as hydraulic or pneumatic motors. The output shaft of the drive unit 185 is coupled, by means of a toothed timing belt 195 and two pulley wheels 200, to the axle of a drive roller 190, which is simply one of the lower rollers 85, thus driving the drive roller 190. Power is then transferred from the drive roller 190 to the annular support 20 by friction between the drive roller 190 and the outer surface 65 of the annular support 20.

The support structure 10 of the illustrated embodiment is designed to operate with an apparatus for supporting and positioning a patient, such apparatus including a detached patient support 205 or bed, an engaged patient support 210 or pallet receiver, and a cylinder support or cylinder 212.

The detached patient support 205 includes rigid patient frame 215 supported by four casters 220. Mounted near the top of the patient frame 215 are first support wheels 225 for supporting a stretcher 227 having a flat lower surface and two parallel sides upon which a patient is lying. Two parallel, spaced apart side rails 230 are rigidly attached to the patient frame 215. The first support wheels 225 and the side rails 230 are arranged to enable the stretcher 227 to roll lengthwise on the detached patient support 205. Thus, if the patient support 205 faces the front surface 70 such that the patient support is central and perpendicular relative to the annular support 20, the stretcher 227 is movable on the first patient support wheels 225 substantially along the axis of the annular support 20. A gear box and motor unit 237 driving at least one of the first patient support wheels 225 moves the stretcher 227 as described. A 0.125 horsepower permanent magnet DC motor has been found to be adequate.

The detached patient support 205 can be used both for transporting a patient to and from the scintillation camera 5 and support structure 10 therefor, and for supporting and positioning a patient relative to the base 15 during operation of the scintillation camera 5 and support structure 10. To ensure that the detached patient support 205 remains stationary during operation of the scintillation camera 5, four brakes 233 can be lowered. Thus lowered, the brakes 233 ensure that the detached patient support remains stationary relative to the floor.

The engaged patient support 210 includes a second rigid frame or rigid base frame 234 and second support wheels 235. The second support wheels 235 are positioned such that the stretcher 227 rolled along the first support wheels 225 can roll onto the second support wheels 235 until the stretcher 227 is either fully or partially supported by the second support wheels 235. The engaged patient support 210 also includes four transverse wheels 240.

The cylinder 212 is rigidly mounted to the annular support 20. The cylinder 212 is aligned with the orifice 60 of the annular support 20 such that the cylinder is coaxial with the annular support 20. The cylinder 212 includes a smooth inner surface 245 upon which rest the transverse wheels 240 of the engaged patient support 210. Thus, the arrangement is such that the patient remains stationary substantially along the axis of the annular support 20 as the annular support 20 rotates relative to the base 15, regardless of whether the board or stretcher is supported by the first support wheels 225, the second support wheels 235, or both.

The engaged patient support 210 also includes a stabilizer 245. The stabilizer 245 includes outside wheels 250 to maintain the engaged patient support 210 horizontal, that is, to stop the engaged patient support from tipping relative to the cylinder 212. The outside wheels 250 roll on the outside surface 243 of the cylinder 212. The stabilizer 245 also includes end wheels 255 to prevent the engaged patient support 210 from moving in a direction parallel to the axis of the cylinder 212. The end wheels 255 roll on the ends 244 of the cylinder 212.

Numerous modifications, variations and adaptations may be made to the particular embodiments of the invention described above without departing from the scope of the invention, which is defined in the claims.

I claim:

1. An apparatus for supporting a patient relative to a scintillation camera, the scintillation camera comprising a vertically oriented annular rotating support having an axis, and an elongate support extending from the rotating support for supporting a detector head, the rotating support comprising a coaxial inner surface defining an orifice, the apparatus comprising:

a patient stretcher for supporting a patient in a horizontal position substantially parallel to the axis of the rotating support;

a detached support for horizontally supporting the patient stretcher on a ground surface and for positioning the patient stretcher relative to the rotating support of the scintillation camera; and an engaged support for horizontally supporting the patient stretcher within the rotating support of the scintillation camera, said engaged support having means for engaging the inner surface of the rotating support such that the patient stretcher and the engaged support are supported by the rotating support and remain horizontal during rotation of the rotating support.

2. An apparatus as defined in claim 1, further comprising a cylindrical support rigidly mountable to the inner surface of the rotating support of the scintillation camera such that the cylindrical support is coaxial with and extends beyond the rotating support.

3. An apparatus as defined in claim 1, the patient stretcher further comprising a flat lower surface and two parallel sides.

4. An apparatus as defined in claim 1, the detached support further comprising:

a rigid frame;

floor rolling means for engaging a ground surface such that the frame is moveable relative to the ground surface; and a brake for immobilizing the frame relative to the ground surface.

5. An apparatus as defined in claim 3, the detached support further comprising:

a plurality of parallel wheels in rolling engagement with the lower surface of the patient stretcher; and a pair of rails slidably engaging the sides of the patient stretcher for stabilizing the patient stretcher.

6. An apparatus as defined in claim 1, the engaged support further comprising a rigid base frame and a transverse rolling means for allowing relative motion between the base frame and the inner surface of the rotating support of the scintillation camera.

7. An apparatus as defined in claim 6, the transverse rolling means comprising a plurality of parallel wheels for orienting perpendicularly to the axis of the rotating support of the scintillation camera.

8. An apparatus as defined in claim 3, the engaged support comprising a plurality of parallel wheels for rolling engagement with the lower surface of the patient stretcher.

9. An apparatus as defined in claim 1, the engaged support further comprising a stabilizer for stabilizing the engaged support relative to the inner surface of the rotating support.

10. An apparatus for supporting a patient relative to a scintillation camera, the scintillation camera comprising a vertically oriented annular rotating support having an axis, and an elongate support extending from the rotating support for supporting a detector head, the rotating support comprising a coaxial inner surface defining an orifice, the apparatus comprising:

a cylindrical support rigidly mountable to the inner surface of the rotating support of the scintillation camera such that the cylindrical support is coaxial with and extends beyond the rotating support, the cylindrical support comprising an inner surface, an outer surface, a circular front edge, and a circular rear edge;

a patient stretcher for supporting a patient in a horizontal position substantially parallel to the axis of the rotating support, the patient stretcher comprising a flat lower surface and two parallel sides;

a detached support for horizontally supporting the patient stretcher on a ground surface, the detached support comprising:
  (a) a rigid frame;
  (b) floor rolling means for engaging a ground surface such that the frame is moveable relative to the ground surface;
  (c) a brake for immobilizing the frame relative to the ground surface,
  (d) a plurality of parallel wheels in rolling engagement with the lower surface of the patient stretcher; and
  (e) a pair of rails slidably engaging the sides of the patient stretcher for stabilizing the patient stretcher;

an engaged support for horizontally supporting the patient stretcher on the inner surface of the cylindrical support such that the patient stretcher remains unaffected by rotation of the rotating support, the engaged support comprising:
  (a) a rigid base frame;
  (b) a transverse rolling means for engaging the inner surface of the cylindrical support, the transverse rolling means comprising a plurality of parallel wheels for orienting perpendicularly to the axis of the rotating support in rolling engagement with the inner surface of the cylindrical support;
  (c) a plurality of parallel wheels for rolling engagement with the lower surface of the patient stretcher; and
  (d) a stabilizer for stabilizing the engaged support relative to the cylindrical support, the stabilizer comprising:
    (i) at least one outside wheel in rolling engagement with the outer surface of the cylindrical support;
    (ii) at least one end wheel in rolling engagement with the front edge of the cylindrical support; and
    (iii) at least one rear end wheel in rolling engagement with the rear edge of the cylindrical support.

* * * * *